US00PP14175P29

(12) United States Plant Patent
Nixon

(10) Patent No.: US PP14,175 P2
(45) Date of Patent: Sep. 23, 2003

(54) ZOYSIAGRASS PLANT NAMED 'SERENE'

(76) Inventor: Ronald Douglas Nixon, 2405 Hwy 82, Midway, AL (US) 36053

( * ) Notice: Subject to any disclaimer, the term of this patent is extended or adjusted under 35 U.S.C. 154(b) by 2 days.

(21) Appl. No.: 10/093,810

(22) Filed: Mar. 11, 2002

(51) Int. Cl.[7] ..... A01H 5/00

(52) U.S. Cl. ..... Plt./390
(58) Field of Search ..... Plt./390

*Primary Examiner*—Bruce R. Campell
*Assistant Examiner*—A Para

(57) ABSTRACT

An asexually reproduced variety of perennial zoysiagrass with a unique combination of characters including fine to medium leaf blade width, low floral production, and unique AFLP fingerprint.

4 Drawing Sheets

Figure 3:
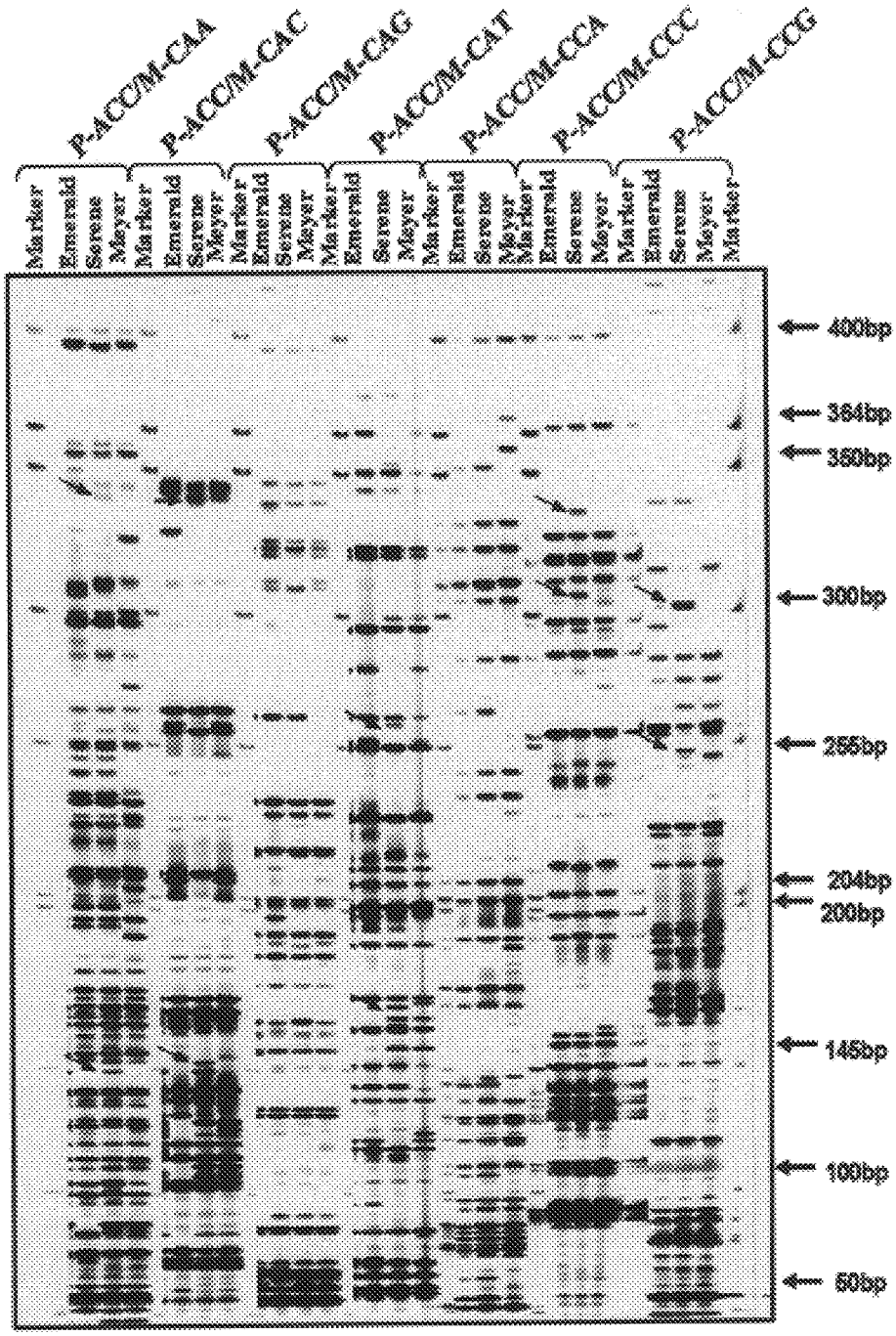

Latin name of the genus and species of the plant claimed: The present invention relates to the genus and species *Zoysia japonica* (L.) Merr.

Variety denomination: 'Serene'.

BACKGROUND OF THE INVENTION

Field of Invention

The present invention relates to a new and distinct asexually reproduced variety of perennial zoysiagrass (*Zoysia japonica* (L.)) Merr.

BRIEF SUMMARY OF THE INVENTION

BACKGROUND OF THE INVENTION

This invention relates to a new and distinct perennial zoysiagrass cultivar identified as 'Serene' zoysiagrass (herein referred to as 'Serene'). The inventor, Ronald Nixon, discovered 'Serene' under cultivated conditions in a sod field near Midway, Ala. 'Serene' was identified as a distinctly different vegetative patch or segregated clonal plant differing by finer leaf texture and softer leaf from the suspected parental variety 'Meyer' (unpatented). The inventor asexually reproduced 'Serene' by taking vegetative cuttings of the plant material from the field including stolons and rhizomes, cutting the rhizomes and stolons into segments, each with a vegetative bud, and rooted them in potting media near Midway, Ala. Another zoysiagrass discovered by Ronald Nixon, the variety 'Marion', is the subject of the co-pending U.S. Patent Application, having application Ser. No. 10/091,876.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'Serene'.

BRIEF DESCRIPTIONS OF THE ILLUSTRATIONS

FIG. 1. Leaf surface of 'Serene' zoysiagrass.

FIG. 2. Tiller of 'Serene' zoysiagrass.

FIG. 3. AFLP fingerprints of 'Serene' and other zoysiagrass varieties generated by six primer combinations, P-ACC/M-CAA, P-ACC/M-CAC, P-ACC/M-CAT, P-ACC/M-CCA, P-ACC/M-CCC, and P-ACC/M-CCG. Arrows mark polymorphic bands showing clear distinction from 'Meyer' and 'Emerald'.

FIG. 4. Inflorescence of 'Serene' zoysiagrass.

COMPLETE DESCRIPTION OF THE VARIETY

'Serene' was characterized in greenhouse and field conditions. 'Serene' is a unique variety of zoysiagrass (*Zoysia japonica* (L.)) Merr. that was discovered under cultivated conditions in a sod field. 'Serene' was identified in the field as having a softer leaf texture than its suspected parent 'Meyer'. The sod field was located in USDA Plant Hardiness Zone 8A. 'Serene' was propagated by the inventor under field and greenhouse conditions in Midway, Ala. by cutting of rhizomes and stolons, rooting them in soil, and planting of the rooted material to provide planting stock for studying performance and for comparison of morphological characters after propagation. 'Serene' has been propagated by rhizomes, stolons, tillers, and sod. Asexually reproduced plants of 'Serene' have remained stable and true to type through successive generations of propagation. No seedling establishment from 'Serene' has been noticed in either greenhouse or field studies.

'Serene' is a perennial zoysiagrass that spreads by both stolons and rhizomes. Characteristics of 'Serene' measured in 2001 were taken from plants approximately six months in age. Characteristics of 'Serene' measured in 2003 were taken from plants that were approximately 15 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'Serene' has a finer leaf texture than the suspected parent 'Meyer', and is finer than 'Crowne' and 'El Toro' (Table 1) with a wider leaf blade than 'Cashmere' (unpatented), 'Diamond', 'Emerald' (unpatented, 'Royal', or 'Cavalier' when measured under greenhouse conditions in Lebanon, Oreg., 2003. 'Serene' has a shorter floral area than 'Meyer', 'Crowne', and 'El Toro', with shorter anthers than 'Meyer' (Table 2). 'Serene' has adaxial surface leaf hairs compared to the varieties 'Cashmere' and 'Royal' that have no leaf hairs. The leaf hairs of 'Serene' are shorter than 'Meyer' and 'Emerald' and 'Marion' (Table 3). 'Serene' has a low floral production compared to 'Emerald' and 'Cashmere' (Table 4), and no seeds of 'Serene' have developed; no seedlings have been noted in the field production area. The inflorescences produced in the greenhouse have consisted of empty glumes and no seed has been formed.

'Serene' has not shown any susceptibility in tests to date in the Midway, Ala. production site to the diseases and insects commpn to the zoysiagrass genus. 'Serene' shows turf density similar to 'Cashmere'. 'Serene' has shown good turfgrass performance and temperature adaptation when tested as far north as Atlanta, Ga., USDA zone 7b, which would extend the area of adaptation for 'Serene' in a line from central Georgia across northern Arkansas through Central to North Texas in an East/West line and on a North/South line from central Georgia south through Mexico. 'Serene' will be limited only by winter survival in colder regions. 'Serene' is similar to most medium to fine textured zoysiagrasses in water use demands as shown in production situations, and will be limited by adequate precipitation in drier to arid regions. 'Serene' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, Oreg. 2003.

| Variety | Width, 2nd youngest stolon leaf mm | Length, 2nd youngest stolon leaf cm | Length, 3rd youngest crown leaf cm | Width, 3rd youngest crown leaf mm | Leaf Texture Class |
|---|---|---|---|---|---|
| 'Serene' | 2.61 | 3.68 | 4.17 | 2.47 | Fine–Medium |
| 'Cashmere' | 1.65 | 3.81 | 3.68 | 1.89 | Fine |
| 'Diamond' | 1.76 | 3.27 | 2.02 | 1.13 | Very Fine |
| 'Emerald' | 1.80 | 2.54 | 4.85 | 2.10 | Fine |
| 'Royal' | 1.88 | 2.60 | 1.92 | 1.63 | Very Fine |
| 'Cavalier' | 2.08 | 3.59 | 2.15 | 1.87 | Very Fine |
| 'Marion' | 2.65 | 3.68 | 4.97 | 2.83 | Fine–Medium |
| 'Meyer' | 2.95 | 3.29 | 6.47 | 3.64 | Medium–Coarse |
| 'Crowne' | 3.39 | 3.96 | 5.40 | 3.85 | Medium–Coarse |
| 'El Toro' | 3.77 | 5.45 | 3.80 | 3.32 | Medium–Coarse |
| t, p = 0.05 | 0.060 | 1.170 | 2.370 | 0.150 | |

TABLE 2

Inflorescence and leaf characters of selected zoysiagrass cultivars, measured under greenhouse conditions in Lebanon, Oreg. 2003.

| Variety | Length floral area cm | Length, flag leaf collar to first lower node mm | Sheath length, crown leaf cm | Anther length mm | Node width at base of inflorescence mm |
|---|---|---|---|---|---|
| 'Serene' | 2.05 | 9.30 | 1.51 | 1.42 | 0.74 |
| 'Emerald' | 1.44 | 4.15 | 1.81 | 1.29 | 0.78 |
| 'Cashmere' | 1.76 | 13.48 | 1.40 | 1.31 | 0.60 |

TABLE 2-continued

Inflorescence and leaf characters of selected zoysiagrass cultivars, measured under greenhouse conditions in Lebanon, Oreg. 2003.

| Variety | Length floral area cm | Length, flag leaf collar to first lower node mm | Sheath length, crown leaf cm | Anther length mm | Node width at base of inflorescence mm |
|---|---|---|---|---|---|
| 'Marion' | 1.98 | 7.27 | 2.14 | 1.49 | 0.72 |
| 'Meyer' | 3.10 | 3.78 | 1.80 | 2.17 | 0.78 |
| 'Crowne' | 3.16 | 9.00 | 1.74 | 3.50 | 0.72 |
| 'El Toro' | 3.78 | 8.38 | 1.53 | 1.50 | 0.99 |
| t, p = 0.05 | 0.128 | 2.710 | 0.131 | 0.010 | 0.013 |

TABLE 3

Internode lengths and adaxial leaf hair length measurements of selected zoysiagrass cultivars, measured under greenhouse conditions in Lebanon, Oreg. 2003

| Variety | Hair length, adaxial leaf mm | Stolon Internode length, node 2–3 cm | Stolon Internode length, node 3–4 cm |
|---|---|---|---|
| 'Serene' | 0.917 | 1.640 | 1.22 |
| 'Marion' | 1.339 | 0.950 | 1.10 |
| 'Emerald' | 2.153 | 1.000 | 1.02 |
| 'Cashmere' | 0.000 | 1.987 | 1.50 |
| 'Meyer' | 1.767 | 1.900 | 2.02 |
| 'Royal' | 0.000 | 1.580 | 1.90 |
| 'Crowne' | 1.247 | 1.800 | 1.52 |
| 'Cavalier' | 2.029 | 1.729 | 1.63 |
| 'El Toro' | 1.263 | 1.350 | 1.00 |
| t, p = 0.05 | 0.080 | 0.126 | 0.12 |

TABLE 4

Floral production of zoysiagrass varieties from greenhouse grown plants, Lebanon, Oreg. November 2001.

| Variety | Flowering Frequency % | Mean Inflorescence Number |
|---|---|---|
| 'Serene' | 0 | 0.0 |
| 'Cashmere' | 100 | 10.3 |
| 'Meyer' | 0 | 0.0 |
| 'Emerald' | 100 | 16.3 |

COMPLETE BOTANICAL DESCRIPTION OF THE VARIETY

Origin.—'Serene' is a cultivar of a single clone discovered under cultivated conditions in Midway, Ala. in a sod field of 'Meyer' zoysiagrass.

Classification.—*Zoysia japonica* (L.) Merr.

Growth habit.—'Serene' is a perennial plant that spreads by stolons and rhizomes and produces a dense, medium to fine textured turfgrass. The inflorescence of 'Serene' is a terminal spike-like raceme, with spikelets on short pedicels.

Leaf blade.—Rolled in the bud, slightly concave surface.

Leaf blade pubescence.—Adaxial leaf surface has few (8–12) hairs approximately 0.92 mm in length; hairs absent on abaxial leaf surface.

Leaf sheath pubescence.—Few long hairs at mouth of sheath approximately 2.69 mm length.

Leaf blade margin.—Rough with small serrations.

Leaf blade veins.—Obscure.

Leaf ligule hairs.—Up to 1.5 mm in length, 5 to 7 in number in center of ligule.

Leaf blade flexibility (softness).—Medium soft.

Vegetative leaf, third youngest vegetative leaf.—*Blade length range:* 1.7 cm to 6.7 cm, mean length: 4.17 cm. *Blade width mean:* 2.47 mm. *Sheath length mean:* 1.51 cm.

Stolon leaf angle, third youngest leaf.—91.3 (Meyer: 98.1; El Toro: 100.6).

Stolon internode length, node 2–3.—1.64 cm.

Stolon internode length, node 3–4.—1.22 cm.

Stolon internode width, node 2–3.—1.13×1.26 mm.

Stolon internode width, node 3–4.—1.15×1.38 mm.

Inflorescence characters.—*Culm total length, including floral area to node below flag leaf*—3.52 cm. Length of stem of inflorescence: 1.47 cm. Floral area length: 2.05 cm.

*Culm width, stem thickness, base of floral area:* 0.74 mm.

*Anther length:* 1.42 mm.

*Floret* (*seed*) *length:* 3.1 mm.

*Floret* (*seed*) *width:* 0.98 mm.

*Number florets per inflorescence:* 20.3.

*Node thickness, node below flag leaf:* 0.99 mm.

*Pedicel length:* 1.92 mm.

*Flag leaf length:* 0.79 cm.

*Flag leaf width:* 1.10 mm.

Mature plant height, including inflorescence.—Marion: 18.8 cm; Meyer: 15.0 cm.

Color notations, vegetative characters, based on The R.H.S. Colour Chart (light quality, photoperiod, and general growth of the plants affect color notations):

*Leaf blade color adaxial leaf surface:* 137A green.

*Leaf blade color abaxial leaf surface:* 137A green.

*Stolon color:* 59A red purple and 144B yellow green.

Color notations, floral characters, based on The R.H.S. Colour Chart (light quality, photoperiod, and general growth of the plants affect color notations):

*Culm stalk:* 144B yellow green.

*Matured spikelet* (*lemma on seed*): 161C greyed yellow.

*Stigma:* 2C yellow.

*Anther color:* 46A red.

Turf quality (rated 1–9, 9 best).—7; 'Meyer': 5; 'El Toro': 4.5.

Turf color (rated 1–9, 9 best).—6; 'Meyer': 5; 'El Toro': 4.

Turf density establishment rating (rated 1–9, 9 best).—6.0; 'Meyer': 4; 'El Toro': 4.

Leaf texture rating (rated 1–9, 9 best).—7; 'Meyer': 4; 'Diamond': 9.

I claim:

1. A new and distinct variety of zoysiagrass plant, substantially as described and illustrated herein, characterized particularly by a unique AFLP fingerprint and combination of morphological characters.

* * * * *